US010617329B2

(12) United States Patent
Mendelsohn

(10) Patent No.: US 10,617,329 B2
(45) Date of Patent: Apr. 14, 2020

(54) PHYSICAL ACTIVITY MONITORING DEVICE AND METHOD OF INDICATING A LEVEL OF PHYSICAL ACTIVITY

(71) Applicant: Steven M. Mendelsohn, Columbia, MD (US)

(72) Inventor: Steven M. Mendelsohn, Columbia, MD (US)

( * ) Notice: Subject to any disclaimer, the term of this patent is extended or adjusted under 35 U.S.C. 154(b) by 228 days.

(21) Appl. No.: 15/891,276

(22) Filed: Feb. 7, 2018

(65) Prior Publication Data

US 2018/0228406 A1 Aug. 16, 2018

Related U.S. Application Data

(60) Provisional application No. 62/457,953, filed on Feb. 21, 2017.

(51) Int. Cl.
*A61B 5/11* (2006.01)
*A61B 5/00* (2006.01)
*A63B 24/00* (2006.01)

(52) U.S. Cl.
CPC .......... *A61B 5/1118* (2013.01); *A61B 5/6822* (2013.01); *A61B 5/742* (2013.01); *A61B 2562/0219* (2013.01); *A63B 24/0062* (2013.01)

(58) Field of Classification Search
CPC ..... G06F 19/34; A61B 5/0205; A61B 5/1118; A61B 5/6822; A61B 5/742; A61B 2562/0219; A63B 220/17; A63B 24/0062
See application file for complete search history.

(56) References Cited

U.S. PATENT DOCUMENTS

| 4,682,378 | A | 5/1987 | Thomis |
| 9,198,621 | B2 * | 12/2015 | Fernstrom ............ A61B 5/1123 |
| 9,211,073 | B2 * | 12/2015 | Banet ................... A61B 5/6831 |
| 9,295,413 | B2 | 3/2016 | Lee et al. |
| 9,456,063 | B2 * | 9/2016 | Mercando ................ H02J 7/32 |
| 9,582,034 | B2 * | 2/2017 | von Badinski .... A61B 5/02416 |
| 9,946,457 | B2 * | 4/2018 | Warren ............... G06F 3/04883 |
| 2009/0054751 | A1 | 2/2009 | Babashan et al. |

(Continued)

FOREIGN PATENT DOCUMENTS

| CN | 202869504 U | 4/2013 |
| WO | 2009061816 A1 | 5/2009 |

(Continued)

OTHER PUBLICATIONS

Fitbit Flex 2 Metal Pendant, Kohls.com, retrieved from Internet Jan. 30, 2018, 4 pages.

(Continued)

*Primary Examiner* — David J. McCrosky
*Assistant Examiner* — Chanel J Jhin

(57) ABSTRACT

According to an embodiment of the present invention, a physical monitoring device is in the form of a necklace or pendant and includes an object (e.g., stone, gem, glass, crystal, or other transparent or translucent object that conveys light signals or color). The physical activity monitoring device includes one or more sensors to measure physical activity or motion of the user (e.g., steps, distance traveled by foot, body motion, etc.). The object is illuminated or changed to different colors to openly and outwardly indicate a level of physical activity of the user.

4 Claims, 11 Drawing Sheets

(56) References Cited

U.S. PATENT DOCUMENTS

| | | | |
|---|---|---|---|
| 2014/0350702 A1 | 11/2014 | Merkel | |
| 2015/0289790 A1* | 10/2015 | Swenson | A61B 5/14539 600/344 |
| 2017/0157466 A1* | 6/2017 | Korpela | A61B 5/0205 |
| 2017/0173262 A1* | 6/2017 | Veltz | A61M 5/1723 |
| 2018/0033919 A1* | 2/2018 | Lee | H01L 33/46 |

FOREIGN PATENT DOCUMENTS

| | | |
|---|---|---|
| WO | 2016044617 A1 | 3/2016 |
| WO | 2016184430 A1 | 11/2016 |

OTHER PUBLICATIONS

MISFIT SHINE2 + HALO NECKLACE (misfit.com) (https://misfit.com/products/misfit-shine-2-halo-necklace), retrieved from Internet on or about Jan. 13, 2017, 4 pages.

Bellabeat LEAF—(amazon.com) (https://www.amazon.com/Bellabeat-LEAF-Tracker-Jewelry-Available/dp/B00XHAEMJU), retrieved from Internet Jan. 12, 2017, 5 pages.

* cited by examiner

PHYSICAL ACTIVITY MONITORING DEVICE AND METHOD OF INDICATING A LEVEL OF PHYSICAL ACTIVITY

CROSS-REFERENCE TO RELATED APPLICATIONS

This application claims priority to U.S. Provisional Patent Application Ser. No. 62/457,953, entitled "Physical Activity Monitoring Device and Method of Indicating a Level of Physical Activity", and filed Feb. 12, 2017, the disclosure of which is incorporated herein by reference in its entirety.

BACKGROUND OF THE INVENTION

1. Technical Area

Present invention embodiments relate to physical activity monitoring devices that indicate varying levels of physical activity by illuminating or changing an object to various colors.

2. Related Art

Various devices may be utilized to measure motion of a user. These device are typically worn on a user arm or wrist. However, the information collected by these devices is discretely conveyed to the user by presenting specific measurements on a display screen. The user may share the measurements by enabling another person to view the display screen, or transfer the measurements to others over a computerized network.

BRIEF SUMMARY OF THE INVENTION

According to an embodiment of the present invention, a physical monitoring device is in the form of a necklace or pendant and includes an object (e.g., stone, gem, glass, crystal, or other transparent or translucent object that conveys light signals or color). The physical activity monitoring device includes one or more sensors to measure physical activity or motion of the user (e.g., steps, distance traveled by foot, body motion, etc.). The object is illuminated or changed to different colors to openly and outwardly indicate a level of physical activity of the user.

BRIEF DESCRIPTION OF THE DRAWINGS

Generally, like reference numerals in the various figures are utilized to designate like components.

DETAILED DESCRIPTION OF EXAMPLE EMBODIMENTS

Present invention embodiments pertain to a physical activity monitoring device preferably in the form of a necklace or pendant, but may be in the form of any desired item of jewelry (e.g., bracelet, necklace, watch, earrings, nose or other ring, etc.) wearable on any desired body portion. The physical activity monitoring device includes an object (e.g., stone, gem, glass, crystal or other transparent or translucent object, etc.) to be illuminated or changed to different colors, and one or more sensors to measure physical activity or motion of the user (e.g., steps, distance traveled by foot, body motion, etc.). The object is illuminated or otherwise changed to different colors to openly and outwardly indicate a level of physical activity of the user. This enables the user to easily share the attained level of physical activity with others for various purposes (e.g., show their level of fitness, competitions, show attainment of fitness goals, etc.).

For example, a physical fitness instructor may easily view the level of fitness of their students wearing the physical activity monitoring device based on the color of the object, and adjust the strenuousness of the workout accordingly and/or determine whether the students are attaining fitness goals. Further, participants of a competition may easily view the status of their competitors, or an individual may simply indicate, or share with others, their level of fitness to build comradery or initiate social encounters or discussions.

Figure 1A:
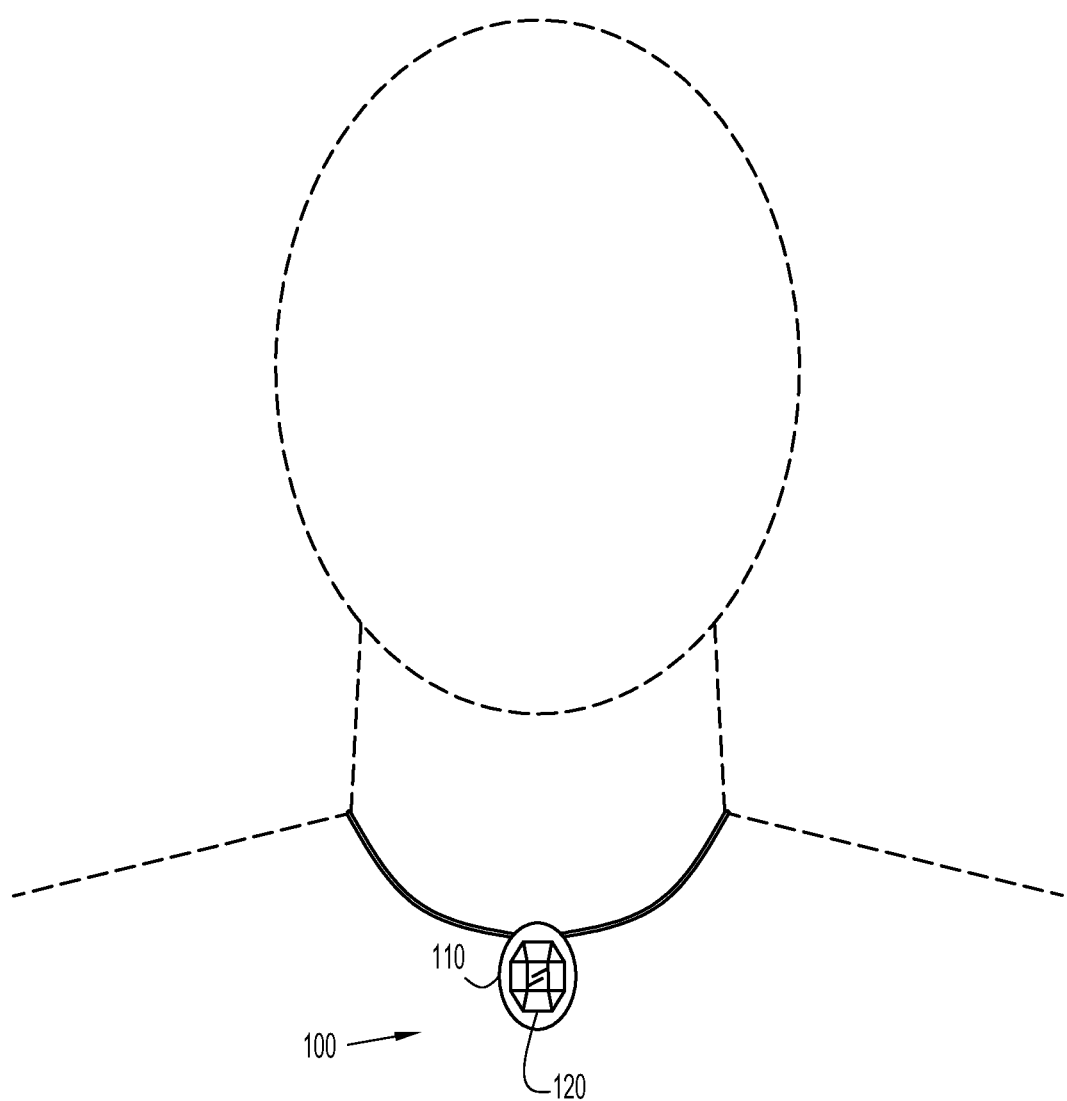
FIG. 1A is a view in perspective of a physical activity monitoring device with an object to be illuminated or changed to different colors to indicate a level of physical activity according to an embodiment of the present invention.

An example physical activity monitoring device according to an embodiment of the present invention is illustrated in FIG. 1A. In particular, physical activity monitoring device 100 is preferably in the form of a necklace or pendant and includes a base or platform 110 and an object 120 secured to the base. A line or chain may engage device 100 (e.g., via a loop or fastener (not shown)) to secure the device to a neck (or other body portion) of a user. Base 100, by way of example, includes an oval configuration, but may be any shape or size (e.g., square or other polygon, circular, amorphous shaped, etc.). The base may be constructed of any suitable materials (e.g., silver, gold, plastics, etc.). Object 120 is secured to the base and may be constructed of any suitable transparent or translucent materials that convey light signals or colors to enable the object to be illuminated or convey varying colors. By way of example, object 120 may include a stone, a gem, a crystal, glass, and/or fiber optic materials. Object 120 is preferably configured with plural surfaces (e.g., to provide an appearance of an item of jewelry). Further, the object may include a body with fiber optic lines or strands extending through the body to convey light signals and illuminate the object.

Figure 1B:
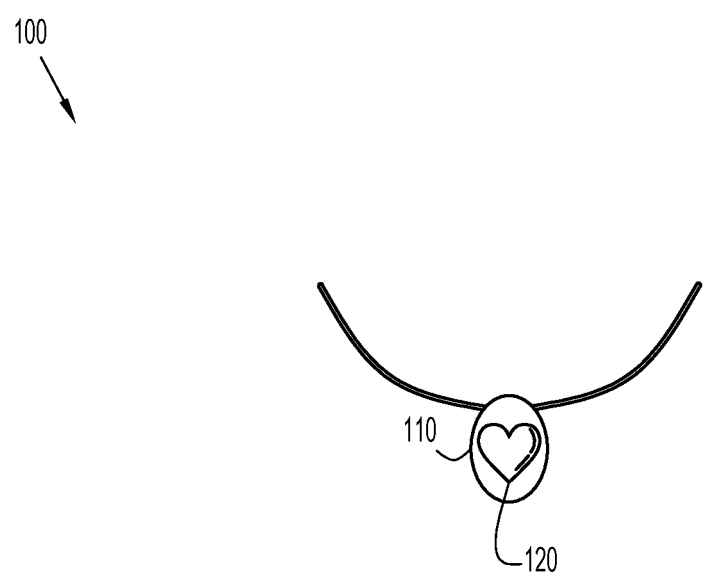
FIG. 1B is a view in perspective of the physical activity monitoring device with a heart-shaped object to be illuminated or changed to different colors to indicate a level of physical activity according to another embodiment of the present invention.
Figure 1C:
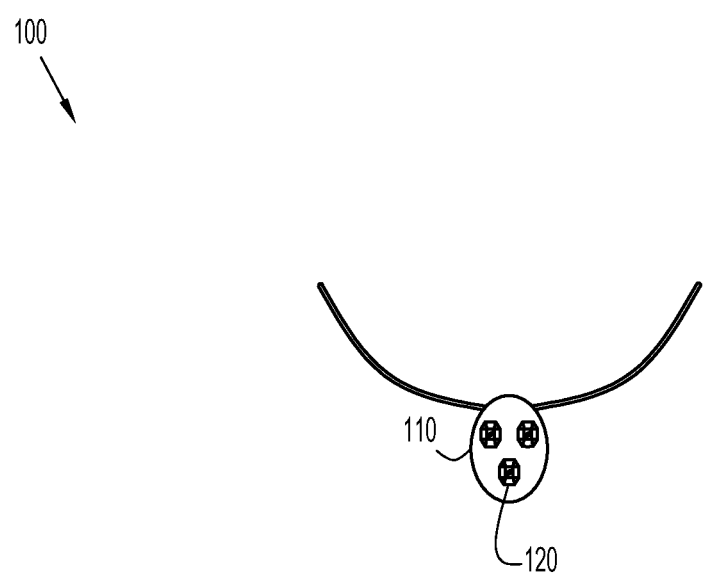
FIG. 1C is a view in perspective of a physical activity monitoring device with a plurality of objects to be illuminated or changed to different colors to indicate one or more levels of physical activity according to an embodiment of the present invention.

In addition, object 120 may include various configurations. For example, the object may be configured in the form of a heart as illustrated in FIG. 1B. Alternatively, the object may be configured in the form of any desired item or symbol (e.g., fitness symbol (e.g., running shoe, etc.), religious symbol, body part, medical symbol, etc.). Further, the object may be configured as one or more items as illustrated in FIG. 1C. For example, object 120 may include a plurality of sub-objects arranged in any fashion on base 100. The sub-objects may each include a stone, a gem, a crystal, glass, and/or fiber optic materials, and be preferably configured with plural surfaces (e.g., to provide an appearance of an item of jewelry). By way of example, object 120 is configured as three sub-objects arranged in a generally triangular fashion. However, any quantity of sub-objects may be employed and arranged in any fashion on the base.

Figure 2:
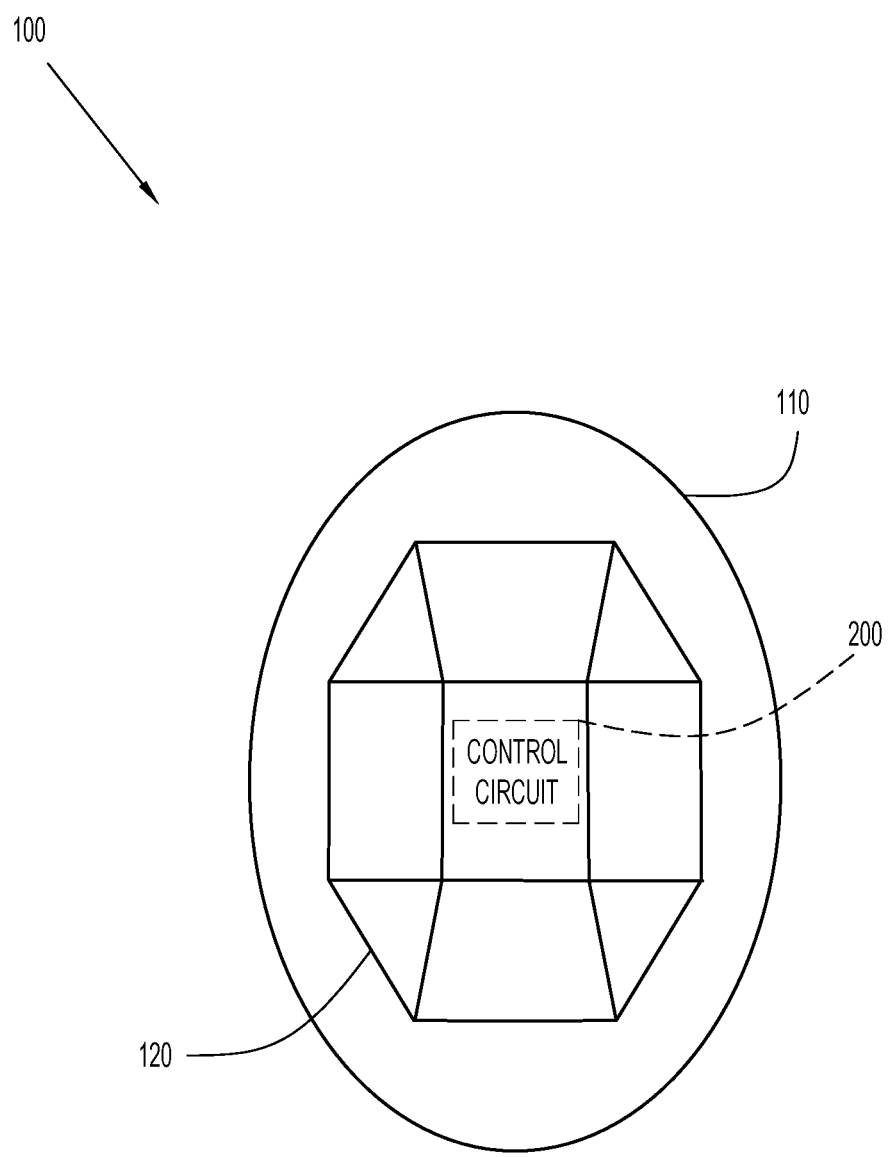
FIG. 2 is a view in perspective of the physical activity monitoring device including a control circuit to measure physical activity and control color change according to an embodiment of the present invention.

Physical activity monitoring device 100 includes a control circuit 200 to measure and indicate physical activity as illustrated in FIG. 2. The control circuit may be disposed between base 100 and object 120 to measure physical activity of the user and control illumination or color change of object 120 as described below. The control circuit illuminates or changes the color of the object in accordance with a sequence or scheme of colors with each color indicating a different level of physical activity (e.g., an amount of motion, a quantity of steps, distances traveled by foot, etc.). The control circuit may be fully or partially mounted to, and/or recessed within, the base, and/or fully or partially secured to, and/or recessed within, the object.

Figure 3:
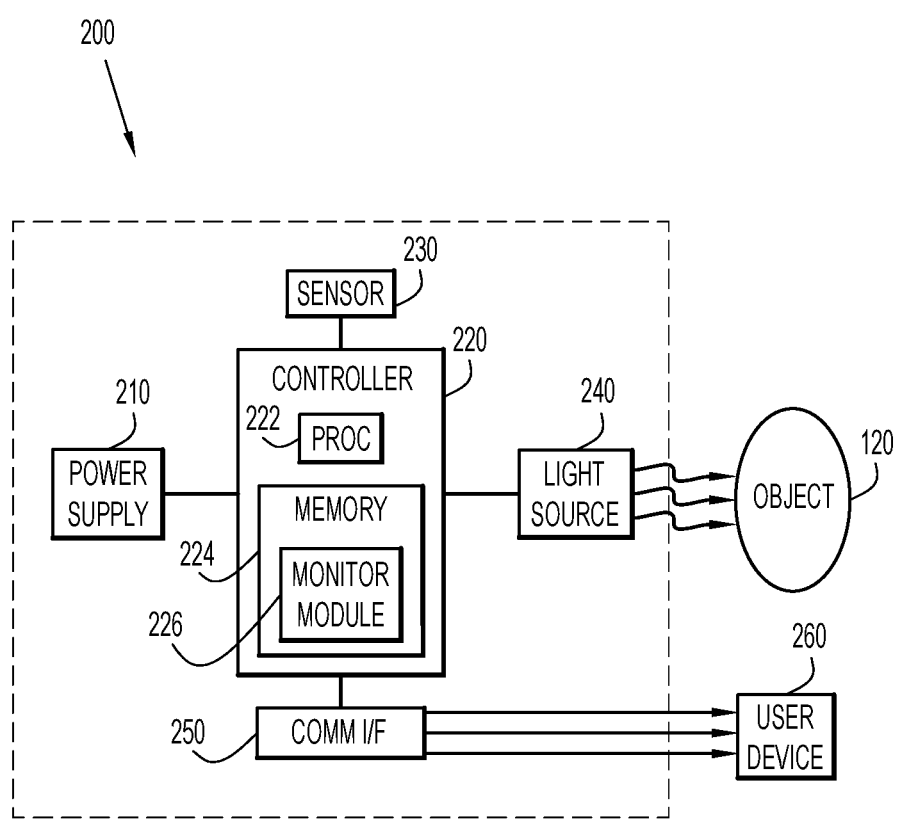
FIG. 3 is a schematic block diagram of the control circuit of FIG. 2 according to an embodiment of the present invention.

An example control circuit according to an embodiment of the present invention is illustrated in FIG. 3. In particular, control circuit 200 includes a power supply 210, a controller 220, one or more sensors 230, a light or color source 240, and a communications interface 250. Power supply 210 provides power to components of control circuit 200, and may include rechargeable or disposable batteries. One or more sensors 230 may include various types of sensors to measure physical activity or motion of a user (e.g., accelerometers, pedometers, etc.). Sensors 230 provide signals indicating the measurements to controller 220. Light source 240 provides light signals of, or changes materials to, various colors to illuminate or change the color of object 120. The light source may include various light elements, materials, and/or components to produce or change the color of object 120 as described below. The control circuit may include any quantity of light or color sources 240 to accommodate any quantity of objects or sub-objects (e.g., each light or color source 240 may illuminate or change the color of any quantity of objects or sub-objects). In addition, light source 240 may provide various effects to the object to further indicate the level of activity (e.g., flash or strobe at any desired rates, adjust brightness, etc.)

Controller 220 receives the measurements from sensors 230 and controls light source 240 to illuminate or change object 120 to an appropriate color based on the sensor measurements as described below. The controller is preferably equipped with a processor 222 and one or more memories 224. The processor may be implemented by any conventional or other microprocessor or controller, and includes a monitor module 226 to process the sensor measurements and control light source 240 to illuminate or change the color of object 120. Monitor module 226 may include one or more modules or units to perform the various functions of present invention embodiments described below. The various modules (e.g., monitor module, etc.) may be implemented by any combination of any quantity of software and/or hardware modules or units, and may reside within memory 224 of controller 220 for execution by processor 222.

The controller may further communicate information pertaining to the user and/or the measured physical activity to a user device 260 via communications interface 250. The communications interface may include any conventional or other communication devices (e.g., transceivers, transmitters, receivers, etc.), and may utilize various communication protocols (e.g., BLUETOOTH, WI-FI, etc.) to communicate directly or indirectly (e.g., over a network) with user device 260. The user device may be implemented by any suitable user computing device (e.g., tablet, laptop or other portable computer, desktop, smartphone or other cellular processing device, etc.). The user device may include an application to receive and process the information from the physical activity monitoring device for presentation to a user utilizing various visualizations (e.g., text, charts, diagrams, calendars, graphical representations, etc.).

Figure 4:
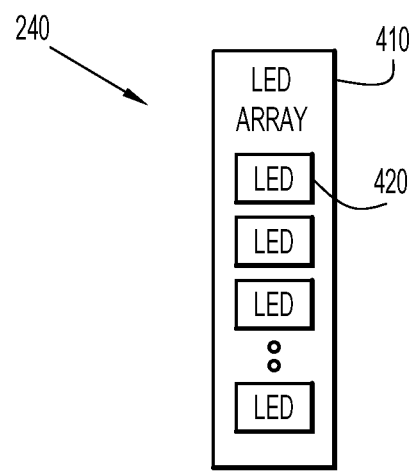
FIG. 4 is a block diagram of the light source of the control circuit of FIG. 3 employing one or more light elements according to an embodiment of the present invention.

Light source 240 may include any suitable devices, elements, or materials to produce color changes or light signals of varying colors (e.g., light emitting diodes (LED), light bulbs, gaseous elements, chemicals, color changing materials, etc.). Referring to FIG. 4, light source 240 may include a light element array 410. The light elements of array 410 may be implemented by one or more light emitting diodes (LED) 420. By way of example, light element array 410 may include one or more multi-color light emitting diodes (LED) 420 each capable of providing various colors of light in accordance with control signals from controller 220. By way of example, a multi-color LED may be implemented by an RGB LED that includes a red LED, a green LED, and a blue LED. Each of the red, green, and blue LEDs may be adjusted to produce a desired color.

Alternatively, each light emitting diode 420 may provide a different color of light, and controller 220 enables the corresponding specific light emitting diodes (LED) of light element array 410 to produce a desired color. The light elements of array 410 may include any suitable devices producing the desired color of light (e.g., light bulbs or filaments, diodes and/or other electronic components, etc.). In addition, any quantity of light elements of the array may be enabled to combine colors to produce other colors (e.g., yellow and blue to produce green, red and yellow to produce orange, etc.).

Figure 5:
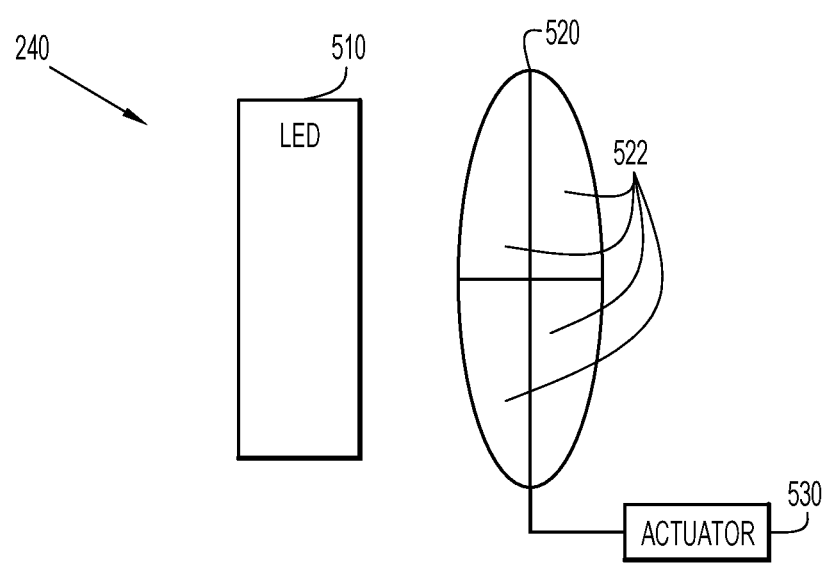
FIG. 5 is a diagrammatic illustration of the light source of the control circuit of FIG. 3 employing a light filter to produce colored light according to another embodiment of the present invention.

Light source 240 may employ a light filter to produce colored light as illustrated in FIG. 5. In particular, light source 240 may include a light element 510, a light filter 520, and an actuator 530. Light element 510 may include any suitable device (e.g., light emitting diode (LED), filament, etc.) to preferably produce white light. Light filter 520 is generally circular and disposed adjacent light element 510. The light filter includes a plurality of sections 522 each associated with a different color filter (e.g., red, green, blue, etc.). Rotation of the light filter is controlled by an actuator 530. The actuator may include any suitable device to control rotation of the light filter (e.g., solenoid, motor, gears, rollers, etc.). Controller 220 determines an appropriate color to be produced by light source 240, and sends control signals to actuator 530. The actuator rotates light filter 520 to a position that aligns color filter 522 of the appropriate color with light element 510. The light produced from the light element traverses the color filter to produce the appropriate colored light to illuminate object 120. The light filter may be of any shape, and include any quantity of color filters associated with any colors. The color filters may include any conventional or other filters to produce (or extract from the light element) the desired color of light. In addition, any quantity of light filters may be used in succession, and/or any color of light may be produced by the light element to combine colors to produce other colors (e.g., yellow and blue to produce green, red and yellow to produce orange, etc.).

Figure 6A:
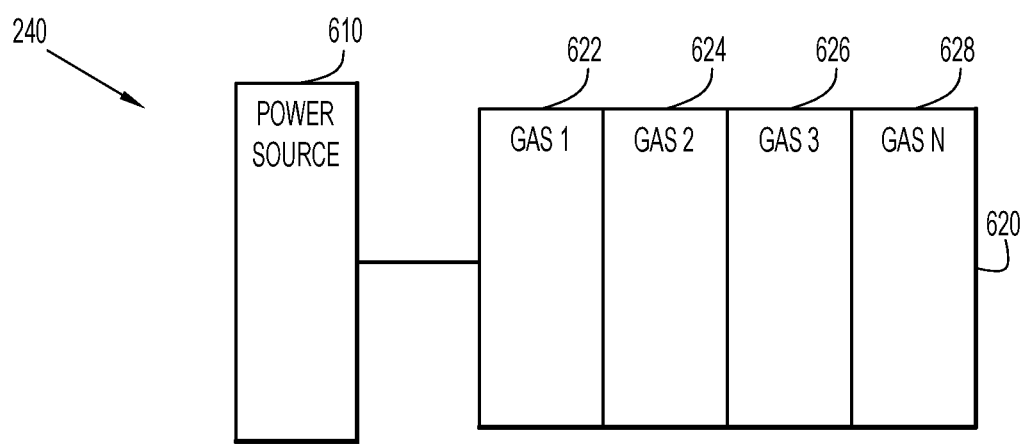
FIG. 6A is a block diagram of the light source of the control circuit of FIG. 3 employing gaseous materials to produce colored light according to yet another embodiment of the present invention.

Light source 240 may utilize materials or chemicals to illuminate or change the color of object 120. For example, light source 240 may excite various gases to produce colored light as illustrated in FIG. 6A. In particular, light source 240 may include a power source 610 and a container 620 including a plurality of compartments or chambers 622, 624, 626, and 628. Each compartment may contain a gaseous element (e.g., Gas 1, Gas 2, Gas 3, to Gas N as viewed in FIG. 6A) that produces a specific color of light when placed in an excited state. Power source 610 may include any suitable power device to excite the gaseous elements in container 620 (e.g., a ballast, etc.). Controller 220 determines an appropriate color to be produced by light source 240, and sends control signals to power source 610. The power source provides appropriate power signals to the compartment having the gaseous element that produces the appropriate colored light. The power signals excite the corresponding gaseous element to produce the appropriate colored light to illuminate object 120. The container may include any quantity of any suitable gases associated with any colors (e.g., neon (orange), hydrogen (red), helium (yellow), carbon dioxide (white), mercury (blue), etc.). In addition, the power source may excite a plurality of gaseous elements to combine colors to produce other colors (e.g., yellow and blue to produce green, red and yellow to produce orange, etc.).

Figure 6B:
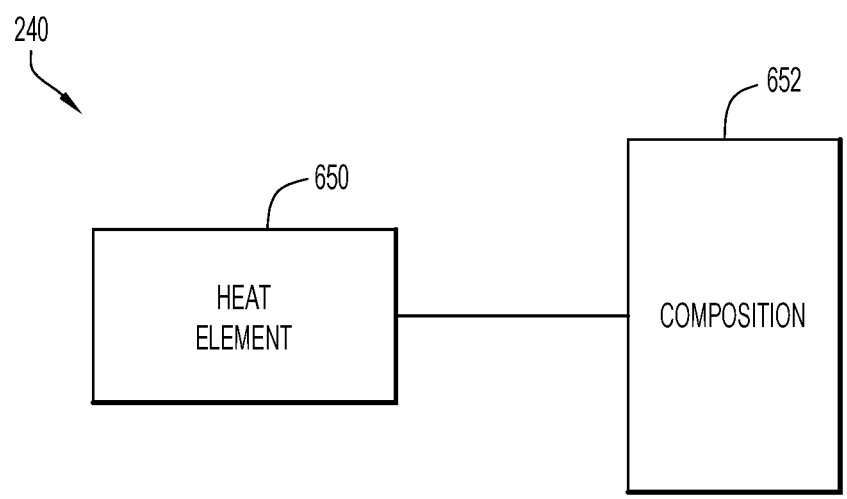
FIG. 6B is a block diagram of the light source of the control circuit of FIG. 3 employing a temperature sensitive color changing material according to still another embodiment of the present invention.

Light source 240 may utilize color changing materials to change the color of object 120 as illustrated in FIG. 6B. In particular, light source 240 may include a heat element 650 and a composition 652. Composition 652 includes materials that change color based on temperature. By way of example, composition 652 may include any thermochromic elements or temperature sensitive color changing materials (e.g., liquid crystals, etc.). Composition 652 may be disposed between heat element 650 and object 120, and may be secured to and/or partially or fully recessed within object 120. Heat element 650 may include any conventional or other heating element (e.g., heating pad, resistive heating element, etc.). Controller 220 determines an appropriate color to be produced by light source 240, and sends control signals to heat element 650 to heat composition 652 to a temperature enabling the composition to change to, or produce, that appropriate color. The composition may include any quantity of materials to produce desired colors. In addition, the light source may include any quantity of heat elements and compositions, where the heat elements may heat various portions of a same composition, or different compositions, to different temperatures to produce a plurality of colors.

Figure 6C:
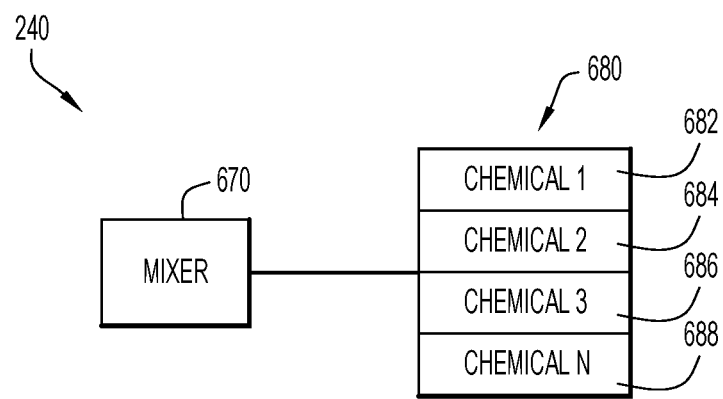
FIG. 6C is a block diagram of the light source of the control circuit of FIG. 3 employing chemicals to produce colored light according to a further embodiment of the present invention.

Light source 240 may combine various chemicals to produce colored light as illustrated in FIG. 6C. In particular, light source 240 may include a mixer 670 and a container 680 including a plurality of compartments or chambers 682, 684, 686, and 688. Each compartment may contain a plurality of chemicals (e.g., Chemical 1, Chemical 2, Chemical 3, to Chemical N as viewed in FIG. 6C) that when combined produces a specific color of light. Mixer 610 may include any suitable mixing device or agitator to combine the chemicals in container 680. Controller 220 determines an appropriate color to be produced by light source 240, and sends control signals to mixer 670. The mixer may manipulate the compartment having the chemicals that produce the appropriate colored light in response to the control signals, thereby mixing the chemicals and producing the desired colored light to illuminate object 120. Further, the mixer may also manipulate the compartments to separate chemicals (e.g., to transition to other colors). The container may include any quantity of any suitable chemicals associated with any colors. In addition, the mixer may manipulate a plurality of the compartments to combine colors to produce other colors (e.g., yellow and blue to produce green, red and yellow to produce orange, etc.).

Figure 7:
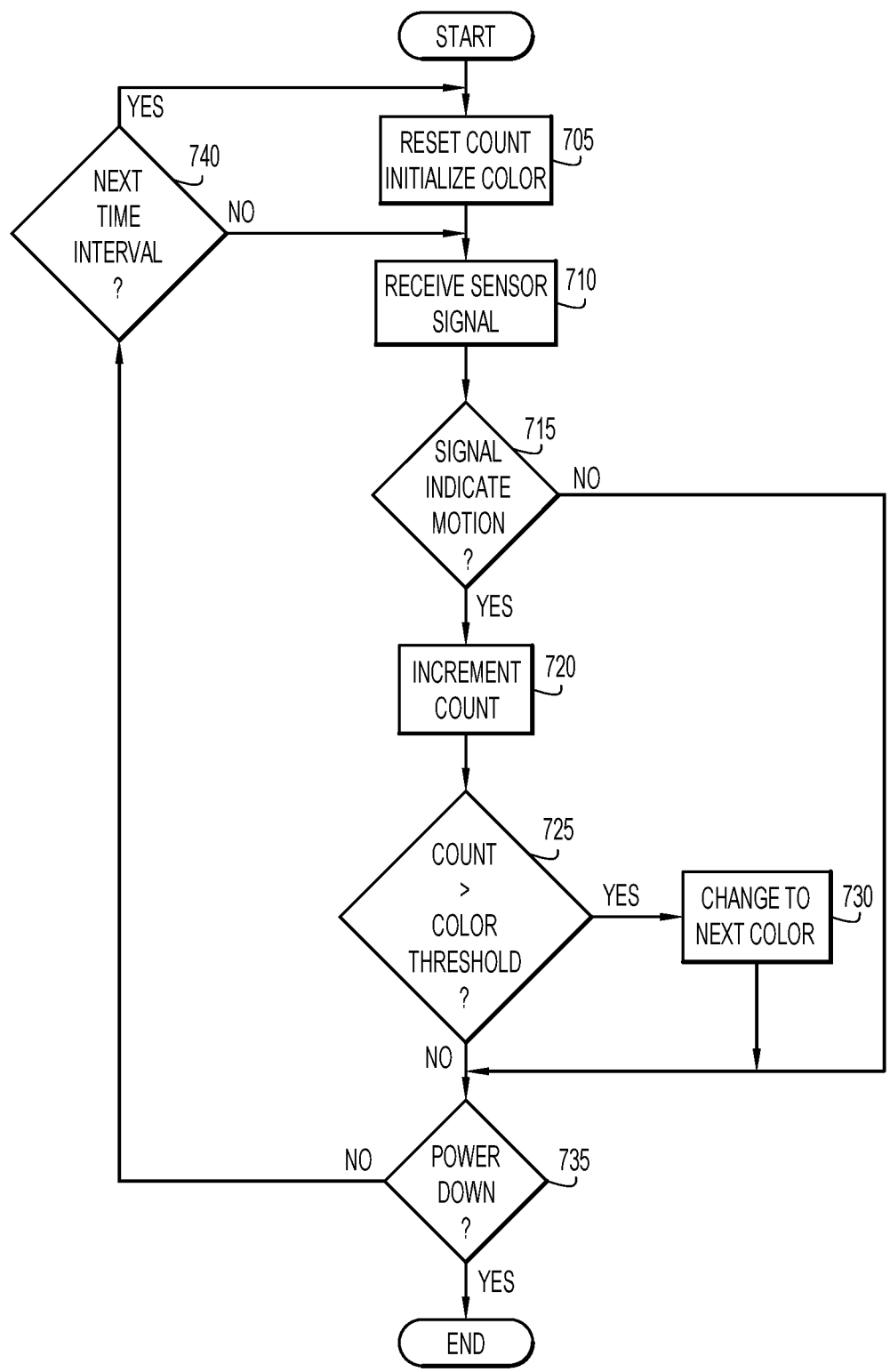
FIG. 7 is a procedural flowchart illustrating a manner of measuring physical activity of a user and illuminating or changing a color of an object to indicate a level of the physical activity according to an embodiment of the present invention.

A manner of measuring physical activity and providing an indication of the level of physical activity of a user (e.g., via controller 220, sensors 230, and monitor module 226) is illustrated in FIG. 7. Initially, the physical activity monitoring device may be configured to measure and provide indications of physical activity over any desired time interval (e.g., hours, days, week, etc.). For example, physical activity may be monitored over an hour for a workout or class, or over a day or week to measure physical activity on a daily or weekly basis. The time interval may be preconfigured or entered by a user (e.g., via user device 260).

In particular, a counter of physical activity occurrences within the time period is initialized, and object 120 is illuminated or set to an initial color at step 705. Sensors 230 measure physical activity and provide measurements to controller 220. The controller receives a measurement at step 710 for processing. The measurements may be provided on a periodic basis (e.g., each second, etc.), or when user physical activity or motion is detected.

The sensor measurement is compared to a threshold at step 715 to determine the presence of a measurement indicating a suitable physical activity. For example, the sensors may provide a measurement in the form of a magnitude of a detected motion. The measurement may be due to a slight movement of a user head or other body portion, instead of a more strenuous physical activity or motion. Accordingly, the threshold is configured to enable a certain degree of physical activity to be identified and contribute to the indication of physical activity. Alternatively, sensors 230 may provide a pulse signal indicating occurrence of a physical activity (e.g., step, etc.).

When the measurement satisfies (e.g., is greater than or equal to, etc.) the threshold to indicate a physical activity as determined at step 715, the counter is incremented at step 720. Alternatively, a count of physical activity (e.g., steps, etc.) may be produced and provided to controller 220 by sensors 230 depending upon the type and/or configuration of the sensors.

The counter value (or count) is compared to a color threshold at step 725 in order to determine conditions for illuminating or changing object 120 to a different color. The physical activity monitoring device employs a color sequence or scheme to indicate the level of physical activity. Each color of the color scheme is associated with a different level of physical activity. For example, the color scheme may transition from shades of blue (e.g., typically associated with colder temperatures or less physical activity) to shades of red (e.g., typically associated with warmer temperatures or greater physical activity) as the amount of physical activity increases and attains various color thresholds (or counts). By way of example, object 120 may be illuminated or changed to: purple for counts less than 2,500; blue for counts between 2,500 and 4,999; green for counts between 5,000 and 7,499; orange for counts between 7500 and 9,999; and red for counts at or exceeding 10,000. However, any color scheme with any quantity of any desired colors and associated count thresholds may be utilized.

When the counter value exceeds a corresponding color threshold as determined at step 725, the controller generates and sends control signals to light source 240 to produce a next color in the color scheme associated with the exceeded threshold at step 730 to illuminate or change the color of object 120. For example: the multi-color or other LEDs 420 of light array 410 may be controlled as described above to produce the next color (FIG. 4); light filter 520 may be manipulated as described above to align a corresponding color filter 522 with light element 510 to produce the next color (FIG. 5); power source 610 may be controlled as described above to excite appropriate gaseous elements in container 620 to produce the next color (FIG. 6A); heat element 650 may be controlled as described above to heat composition 652 to a temperature corresponding to the next color (FIG. 6B); and/or mixer 670 may be controlled as described above to mix and/or separate appropriate chemicals in container 680 to produce the next color.

If the measurement does not satisfy (e.g., is less than, etc.) the threshold as determined at step 715 (e.g., thereby indicating insignificant motion), the count does not exceed the color threshold as determined at step 725, or the color is changed at step 730, the expiration of the time interval is determined at step 740 in response to the physical activity monitoring device remaining active as determined at step 735. When the time interval has expired, the counter is initialized and the object is illuminated or set to the initial color of the color scheme at step 705 as described above. If the time interval has not expired, a next sensor measurement is processed at step 710 as described above.

The above process is performed until power down of the physical activity monitoring device (e.g., user power switch, time out from inactivity, etc.) as determined at step 735.

The software (e.g., monitor module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The controller of the present invention embodiments may alternatively be implemented by any type of hardware and/or other processing circuitry. The various functions of the controller may be distributed in any manner among any number of software and/or hardware modules or units. The software of the present invention embodiments (e.g., monitor module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The physical activity monitoring device may be implemented by any suitable jewelry item, and may be wearable on any desired body portion. The device may employ any quantity of any types of sensors (e.g., accelerometer, pedometer, etc.) to measure any physical activity or motion. The light source may employ any desired components (e.g., electronic, chemical, materials, gases, etc.) to produce any desired colors to illuminate or change the color of any desired object. The object may include any desired object that by itself or with components presents a change in color (e.g., stone, gem, crystal, object with fiber optic properties or materials to convey light, lenses to magnify or present color change, mirrors to reflect color change to the object, diffusers, collimators, etc.). The color scheme may include any quantity of any desired colors ordered in any fashion, where the thresholds may be set for any desired levels of activity (e.g., steps, distance, etc.). The level of physical activity or motion to be considered as an occurrence may be set to any desired level (e.g., strenuous, intermediate, mild, etc.). The physical activity monitoring device may communicate with any desired user computing devices via any suitable communication or other protocols (e.g., wired or wireless connection, etc.).

What is claimed is:

1. A method of measuring and indicating a level of physical activity comprising:
    measuring physical activity of a user via a necklace including an activity sensor and a stone, wherein the physical activity includes exercise of the user, wherein the activity sensor includes an accelerometer and/or pedometer;
    determining a quantity of occurrences of the physical activity based on measurements from the activity sensor; and
    changing an appearance of the stone to a plurality of different colors based on the quantity of occurrences satisfying corresponding thresholds, wherein each threshold is associated with a corresponding one of the different colors.

2. The method of claim 1, wherein the quantity of occurrences of the physical activity includes steps taken.

3. The method of claim 1, wherein the appearance of the stone resets to its initial color after a set period.

4. The method of claim 1, further comprising providing a power source that is rechargeable or replaceable.

* * * * *